(12) United States Patent
Hakky et al.

(10) Patent No.: US 6,500,154 B1
(45) Date of Patent: Dec. 31, 2002

(54) INTRAVASCULAR ACCESS DEVICE POSITIONING SYSTEM

(75) Inventors: Said Ismail Hakky, Largo, FL (US); Jeffrey H. Kuch, Largo, FL (US)

(73) Assignee: Canox International Ltd., Largo, FL (US)

( * ) Notice: Subject to any disclaimer, the term of this patent is extended or adjusted under 35 U.S.C. 154(b) by 0 days.

(21) Appl. No.: 09/480,791

(22) Filed: Jan. 11, 2000

(51) Int. Cl.[7] .................................................. A61M 5/32
(52) U.S. Cl. ....................................... 604/174; 604/179
(58) Field of Search ............................... 604/174, 179, 604/180; 128/877

(56) References Cited

U.S. PATENT DOCUMENTS

| | | | | |
|---|---|---|---|---|
| 3,722,508 A | * | 3/1973 | Roberts | 128/877 |
| 3,812,851 A | * | 5/1974 | Rodriguez | 128/877 |
| 4,425,913 A | | 1/1984 | Lewis | |
| 4,502,477 A | | 3/1985 | Lewis | |
| 4,505,270 A | | 3/1985 | Miles | |
| 4,870,976 A | * | 10/1989 | Denny | 128/877 |
| 4,898,587 A | | 2/1990 | Mera | |
| 4,976,698 A | | 12/1990 | Stokley | |
| 5,084,026 A | | 1/1992 | Shapiro | |
| 5,339,834 A | * | 8/1994 | Marcelli | 128/877 |
| 5,413,120 A | * | 5/1995 | Grant | 128/877 |
| 5,577,516 A | * | 11/1996 | Schaeffer | 128/877 |
| 5,601,597 A | | 2/1997 | Arrowood et al. | |
| 5,749,840 A | | 5/1998 | Mitchell et al. | |
| 5,827,230 A | * | 10/1998 | Bierman | 604/174 |
| 6,113,577 A | * | 9/2000 | Hakky et al. | 604/174 |

* cited by examiner

Primary Examiner—Anhtuan T. Nguyen
Assistant Examiner—Kevin C. Sirmons
(74) Attorney, Agent, or Firm—Rosenberg, Klein & Lee

(57) ABSTRACT

An apparatus for maintaining an intravascular access device in position at an access point on a limb of a patient includes a needle immobilizing unit engaging the needle member and preventing it from dislodgement from the blood vessel, a tube locking member locking the connecting tube in place and preventing it from being separated from the needle member, and a strap which supports the needle immobilizing unit and the locking member immovably on the limb of a patient. For further support of the apparatus in place, a splint assembly is provided which includes two splint members, forearm splint member which is secured to the forearm part of the limb and arm/hand splint member which is securable to either the arm or hand of the limb. The splint members can be used separately or coupled to each other; joint between the splint members has a latching mechanism allowing to adjust the angle between the forearm and arm/hand splint members. The strap carrying the needle immobilizing unit and the tube locking member is secured to a splint member and facilitates in securing the splint.

12 Claims, 10 Drawing Sheets

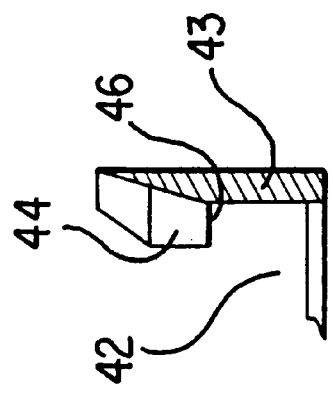
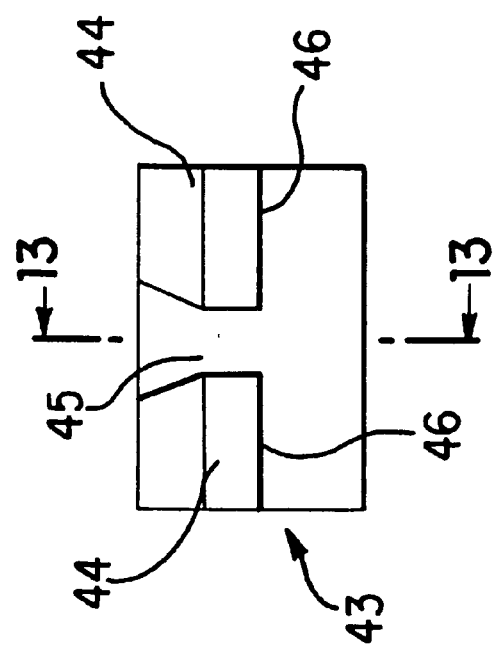

INTRAVASCULAR ACCESS DEVICE POSITIONING SYSTEM

BACKGROUND OF THE INVENTION

FIELD OF THE INVENTION

The present invention relates to surgical equipment, and more particularly, to a device for maintaining intravascular access devices, such as needles, tubes, and catheters in fixed position while administering intravascular therapy, wherein the risk of accidental dislodgement of the intravascular access device during the therapy is minimized substantially.

More particularly, the present invention relates to a structure for immovably maintaining an intrasvascular access device in fixed position on a limb of a patient, with the structure including a needle immobilizing unit and a tube locking member securing a connecting tube of the intravascular access device in fixed position to the needle member. The needle immobilizing unit includes a substantially transparent shield covering the needle member that allows immediate visual recognition of any dislodgement of the intra-vascular access device whenever such may occur.

Further, the present invention relates to a hemodialysis and vascular splint which conveniently and comfortably supports intravascular access devices at a patient's extremity for an extended period of time which is required by certain intravascular therapies including hemodialysis. More particularly, the present invention relates to a splint which comprises two independent members assemblable and easily separable each from the other so that each may be used independently or in combination dependent upon the specific procedure.

The present invention also relates to a splint for supporting intravascular device(s) in fixed position which includes one or two separable splint members where each is affixed to a respective body part by at least one strap which is slidable along the splint member and whose length is adjustable. The splint also maintains an intravascular access device (the needle member and the connecting tube) thereon in the locked position thereby preventing unwanted dislodgement of the intravascular access device during therapy.

PRIOR ART

In the field of surgery, intravascular access devices are widely used for many purposes. For example, the vascular access can be venous when fluids, such as medicine or supporting fluids, are desired to be given to a patient undergoing a surgical procedure. In medical emergencies, intravenous access may be needed to administer fluids, antibiotics, and other medication especially when the patient cannot ingest such through the mouth.

Another type of vascular access, arterial access, is needed to monitor the patient's blood gases and may be used for monitoring his or her vital signs. Patients on hemodialysis may need intravascular access two to three times each week for a period of three hours or longer.

If a needle is dislodged in any of these procedures, and the dislodgement goes unnoticed, severe bleeding may occur. In such instances, the patient may lose a large amount of blood before the medical personnel recognizes the emergency situation. In some cases where the patient is heparinized, i.e., blood is prevented from clotting, the patient may bleed to death, unless the bleeding is recognized and stopped. In hemodialysis, the blood loss in such emergency situations could be as high as several hundred millimeters each minute.

In order to impede separation of the connecting tube from a needle of the intravascular access device, traditionally, strips of tape are applied to a patient's limb which secures the connecting tube and the needle in the proper position on the patient's body. Disadvantageously, this technique abrades hair and skin of the patient in the contact areas and in some instances, may cause serious unwanted skin reaction.

Several attempts have been made in the art to develop a technique which would prevent the vascular bleeding when intravascular access is desired. For example, U.S. Pat. No. 5,601,597 describes the combination radial artery occluder and wrist splint used to simultaneously immobilize the wrist joint and prevent blood flow through a puncture wound or incision in the radial artery following an invasive medical procedure, such as catheterization. The device generally includes three components: a wrist splint that extends along the distal end of the patient's forearm and the back of the wrist and hand; an adjustable pressure strap attached to the splint that extends around the distal end of the forearm; and an adjustable securing strap attached to the splint that extends around the palm of the patient's hand. The pressure strap includes a pressure pad that is selectively positioned to occlude blood flow through only the radial artery, while allowing blood flow through the ulnar artery. During use, the securing strap is tightened around the palm of the hand to help immobilize the wrist joint. The adjustable pressure strap is slowly tightened onto the forearm or wrist over the wound until radial artery blood flow has stopped at the wound. Although intended for stopping blood from punctured arteries, this device is not contemplated for use during the intravascular access procedure, and therefore, no means are envisioned for securing an intravascular access device to the patient's limb.

A prior art splint for use with intravenous lines is described in U.S. Pat. Nos. 4,425,913 and 4,502,477. The splint supports the hand, wrist, and at least a portion of the forearm of a patient during the time, when the patient is connected to a lifeline, e.g., intravenous tube. The splint incorporates a substantially rigid molded body defining several shapes. A dome is provided for mating engagement with the palm of the hand and a tranversely arcuate curved channel extends away from the dome to receive the wrist and a portion of the forearm. The molded body defines securing means for the lifeline, as in the form of rolled or beaded edges of the body which also add strength and rigidity. The molded body is to be physically attached to a patient by the straps, with a hand strap extending somewhat diagonally in relation to the dome, while a pair of forearm straps extend laterally from the opposed side of the molded body. The length of the straps is adjusted by a Velcro type contact fastening member. In use, after the splint is positioned onto the patient and the molded body is secured in place with the contact straps, the intravenous lifeline is connected with the tube anchored in a channel extending along the edges of the molded body. As is readily understandable for those skilled in the art, this splint is intended merely as a support to immobilize the forearm and hand of the patient during intravenous therapy and also as a support for a lifeline, i.e., connecting tube through which liquid is supplied to a needle or a catheter. Disadvantageously, no means are contemplated which would secure the connecting tube to the needle introduced into the blood vessel.

Therefore, in such prior art, a dangerous, undesirable disconnection of the lifeline from the needle may occur. It is a further drawback of the splint described in the previous paragraphs that it is not designed for use as a support for a needle or catheter inserted into the blood vessel of a limb. As a further disadvantage, it may be recognized that different sizes of the splint are generally desirable to accommodate the physical dimensions of different patients, as well as different dimensional needs for the right and the left limbs of the same patient which may require different splints.

A fluid administration splint is also described in U.S. Pat. No. 4,505,270. This splint is intended as a shield for a catheter taped to the leg of an animal. The splint includes an extendable splint member hinged to an extendable cover for accommodating different lengths of a leg, and a latch for securing the splint assembly to a door of a cage containing the animal receiving intravenous fluid. Similar to the splint described in previous paragraphs, the fluid administration splint shown in this prior art is merely a support to immobilize the limb during intravenous therapy.

As it is readily appreciated by those skilled in the art, none of the splints discussed in the previous paragraphs contemplates any means which would secure the needle or a catheter, immovably with respect to its connecting tube during the intravascular access therapy. Further, none of them are intended for use with the arm part, forearm part, and/or the hand of the patient, in combination or individually.

Therefore, despite numerous attempts in the field of surgery to provide means or technique which would reliably secure the intravascular access device in position, no satisfactory technique has been developed to date prior to the subject system.

SUMMARY OF THE INVENTION

It is an object of the present invention to provide a device for supporting an intravascular access device in position during a therapy while the needle of the intravascular access device is introduced into the blood vessel, whereby the needle is prevented from being dislodged from its position and from being separated from a connecting tube.

It is a further object of the present invention to provide a device for supporting the intravascular access device in position at any portion of the upper limb of a patient undergoing a therapy, i.e., hand, arm part, or forearm part of the upper limb.

It is still a further object of the present invention to provide a device for supporting the intravascular access device in position on the upper limb during an intravascular procedure, which is substantially universal for any size or gender of patient.

It is still a further object of the present invention to provide a splint for supporting an intravascular access device in fixed position which includes one or two separable independent splint members each of which is securable to a respective part of the upper limb of the patient and which further can be used independently or in combination with each other, thus providing a flexible and universal splint.

It is still another object of the present invention to provide a splint for supporting the intravascular access device in position on the upper limb of the patient in which each splint member is secured to a respective part of the upper limb of the patient by at least one strap slidable along the longitudinal axis of the splint member to occupy the precise position proximal to the point of intravascular access. The length of each strap is adjustable and each strap carries a needle immobilizing unit with a tube locking member for securing the connecting tube to the needle. In this manner, the connecting tube cannot be dislodged from the needle inserted into the blood vessel.

It is yet a further object of the present invention to provide a splint for supporting an intravascular access device in fixed position which includes a needle immobilizing unit displaceable along and around the respective part of the upper limb of the patient which is positioned in close proximity to the point of the needle access into the blood vessel. The access device secures the needle in place and locks the connecting tube to the needle for the period of time needed to perform a surgical procedure or therapy.

It is another object of the present invention to provide a splint for supporting the intravascular access device in position on the upper limb of the patient, wherein each splint member is secured to a respective part of the upper limb of the patient by individual straps, the length of each is individually adjustable.

It is yet another object of the present invention to provide a splint for supporting the intravascular access device in position, where the arm and forearm splint members (or the forearm and hand splint members) are pivotally connected to each other and where an elbow joint between the arm and forearm splint members (or a wrist joint between the forearm and hand splint members) can lock these members angled to each other at varying angles, i.e., 90°, 180°, 220°, etc., for further convenience and comfort of the patient.

In accordance with the present invention, an apparatus for maintaining intravascular access device in position at an access point on a limb of a patient includes a needle immobilizing unit and a tube locking member carried on a supporting structure which supports the needle immobilizing unit in close proximity to the access point on the limb of the patient.

During the therapy, the needle immobilizing unit engages the needle member and locks the same in place, thereby preventing the needle member from dislodgement from the blood vessel. The tube locking member locks the connecting tube of the intravascular access device in place, thereby preventing the connecting tube from being separated from the needle member.

Preferably, the supporting structure constitutes a strap member encircling a respective part (arm, forearm, or hand) of the limb of the patient. The length of the strap member is adjustable for substantially matching a circumference of the respective portion of the limb of the patient.

The needle immobilizing unit includes a transparent shield secured to the strap member which has a semicylindrical central portion extending longitudinally along the substantially transparent shield and a pair of fans extending symmetrically from the center portion of the transparent shield. The fans engage the skin on the limb of the patient during the therapy while the central portion of the transparent shield receives the intravascular access device therewithin. It is important that locking wings extend at the proximal ends of the fans to engage the needle wings of the intravascular access device, thereby preventing the needle member from being dislodged from the blood vessel.

The substantially transparent shield allows the medical personnel to observe any bleedings which may occur at the access point on the limb of the patient during the therapy and thus to allow necessary measures to be taken.

Preferably, a plurality of holes are disposed across the surface of the transparent shield to permit ventilation.

The tube locking member is affixed on the strap member a predetermined length from the needle immobilizing unit. The tube locking unit has either a clip type structure or a tube housing unit which has a bottom portion and a top portion pivotally joined each to the other at one end thereof and having latching mechanism at another end thereof. When the top and bottom portions of the tube housing unit are latched, a tube receiving channel is formed therein extending laterally through the tube housing unit, so that the connecting tube is impeded from decoupling from the needle member of the intravascular access device. Preferably, fine teeth are provided within the tube receiving channel to fixedly hold the connecting tube.

Optionally, the tube housing unit may have two tube receiving channels of differing cross-sectional dimensions for receiving connecting tubes of different sizes.

From another aspect, the present invention is a splint assembly which comprises two independent splint members pivotally coupled to each other and easily separable from each other. The splint members can be used independently or in joint arrangement. One splint member may be secured to the forearm part of the limb of the patient while the second splint member may be secured either to the arm part of the limb of the patient or to the hand of the patient.

Each splint member has slots extending longitudinally along the length thereof, and one or more straps sliding along the longitudinal slots. Each strap has an adjusting mechanism so that the length of the strap can be adjusted to correspond exactly to the circumference of the limb of the patient.

There are two basic kinds of straps used with the splint assembly of the present invention. One type, which is a supporting strap, serves to support the splint member on the respective part of the limb of the patient. Another type of the strap carries a needle immobilizing unit and tube locking member thereon, and serves the two fold purpose of immobilizing the intravascular access device in position and simultaneously supporting the splint member at the respective part of the limb of the patient.

At the joint between two splint members a joint assembly is provided which releasably pivotally couples the splint members to each other. The joint assembly includes a latching mechanism locking the splint members in a desired angled relationship therebetween. For example, the splint members may be locked at 90° at the elbow joint when used for the arm/forearm parts of the limb of the patient. When used for the forearm/hand parts of the limb of the patient, the splint members can be locked at 200° with respect to each other.

Another aspect of the present invention directs itself to a method for maintaining an intravascular access device in position at an access point on a limb of a patient during therapy. According to this method, a strap member carrying a needle immobilizing unit and a tube locking member is positioned at a respective part of the limb of the patient to encircle this respective part adjacent to the access point of the blood vessel.

The length of the strap member is adjusted to match the circumference of the part of the limb of the patient. The needle member of the intravascular access device is then locked in position while being introduced into the blood vessel by means of the needle immobilizing unit which has locking wings engaged with the needle wings. After this, the connecting tube is locked within the tube locking unit carried on the strap member.

Optionally, one or more splint members can be secured to the limb of the patient by the strap member carrying the needle immobilizing unit and the tube locking member.

If two splint members are used, before being attached to the limb of the patient, the splint members are coupled each to the other at respective ends thereof.

Preferably, the method further includes the steps of latching the first and second splint members in a desired angular relationship which optimizes comfortability of the patient undergoing the therapy.

These and other novel features and advantages of this invention will be fully understood from the following detailed description and the accompanying Drawings.

BRIEF DESCRIPTION OF THE DRAWINGS

FIG. 12 shows somewhat on an enlarged scale a mating part of the latching mechanism taken along Lines 12—12 of FIG. 9;

FIG. 13 is a cross-section of the vertical wall of the tube housing unit taken along Lines 13—13 of FIG. 12;

DETAILED DESCRIPTION OF THE PREFERRED EMBODIMENT

Figure 1:
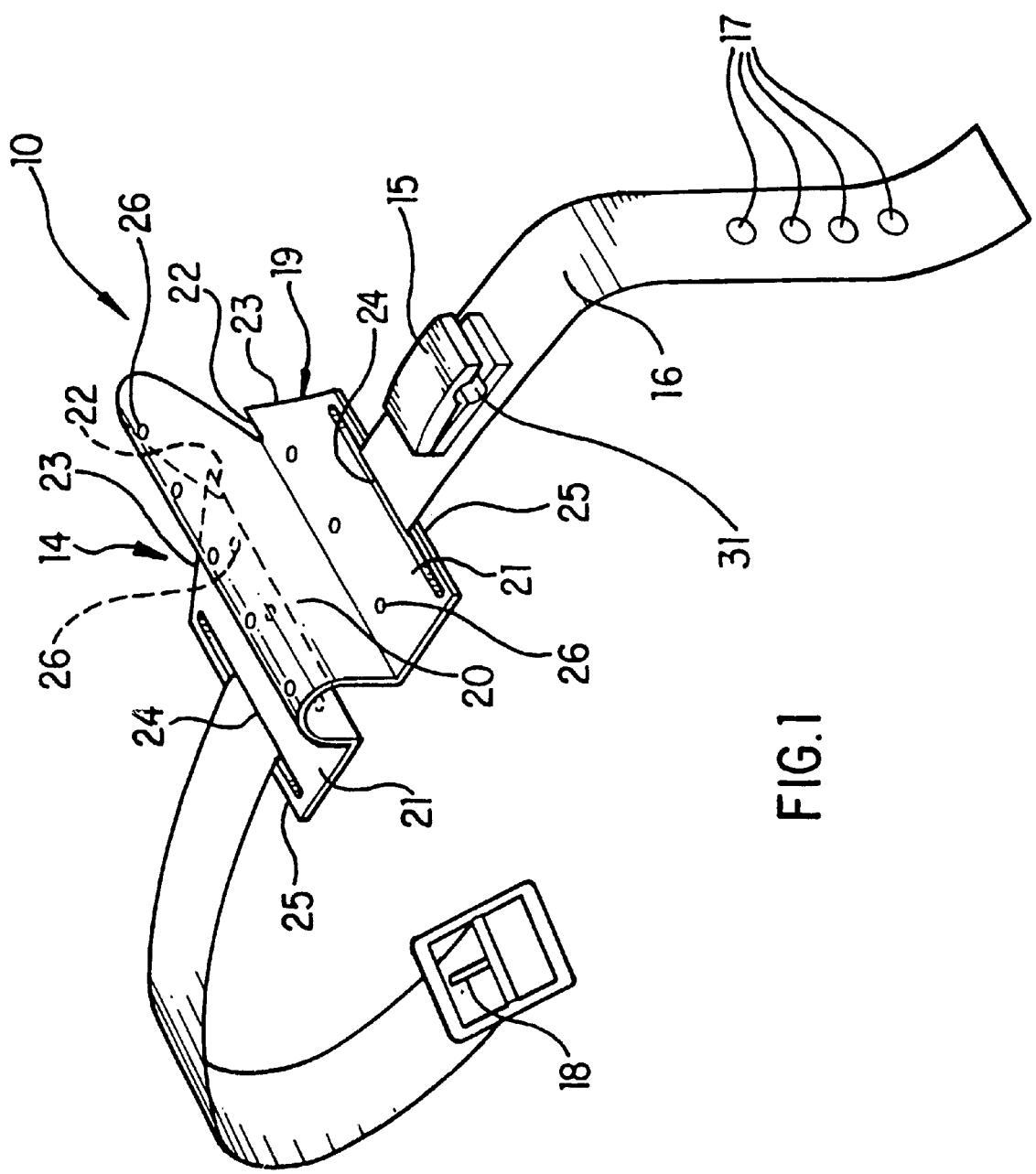
FIG. 1 is a perspective view of a strap member of the present invention carrying a needle immobilizing unit and a tube locking member thereon.
Figure 2:
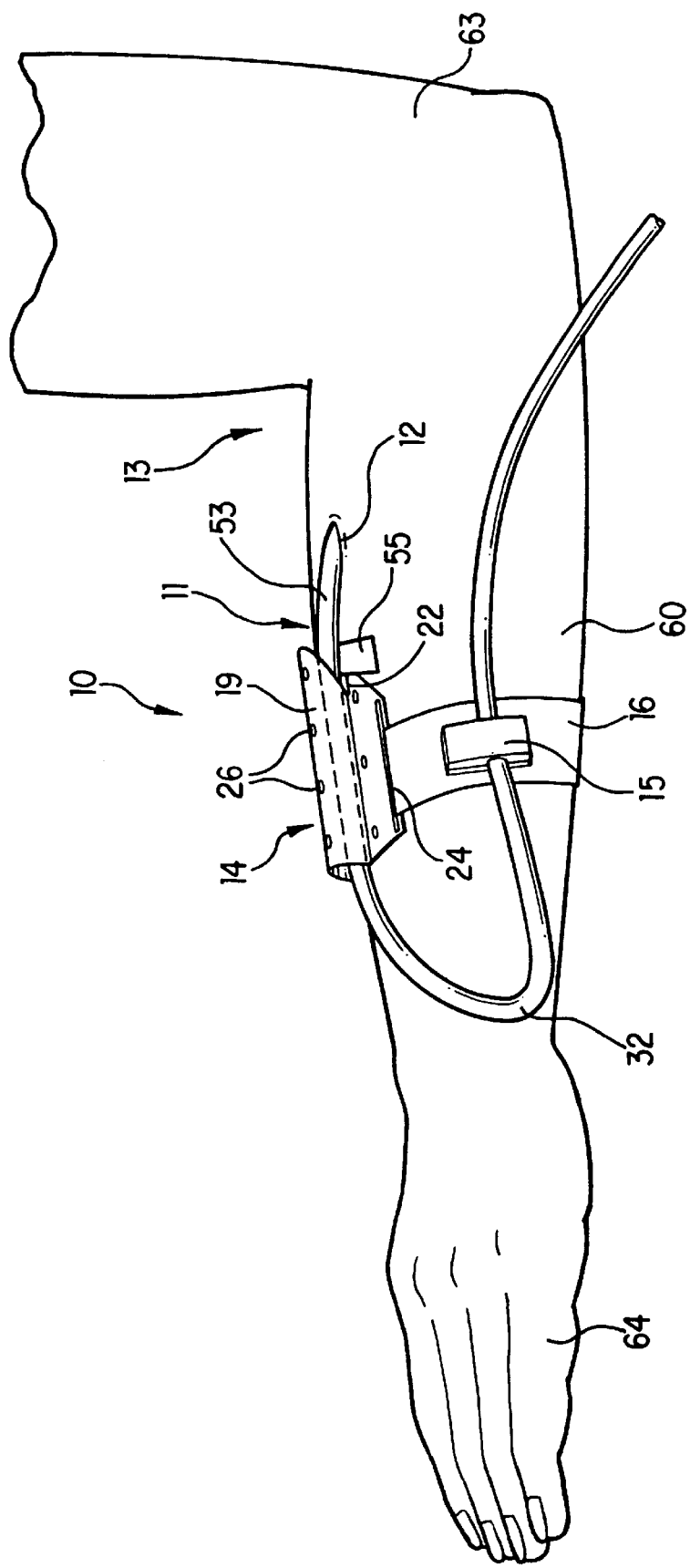
FIG. 2 is a pictorial view illustrative of the apparatus of the present invention secured to the forearm of the patient during therapy.
Figure 3:
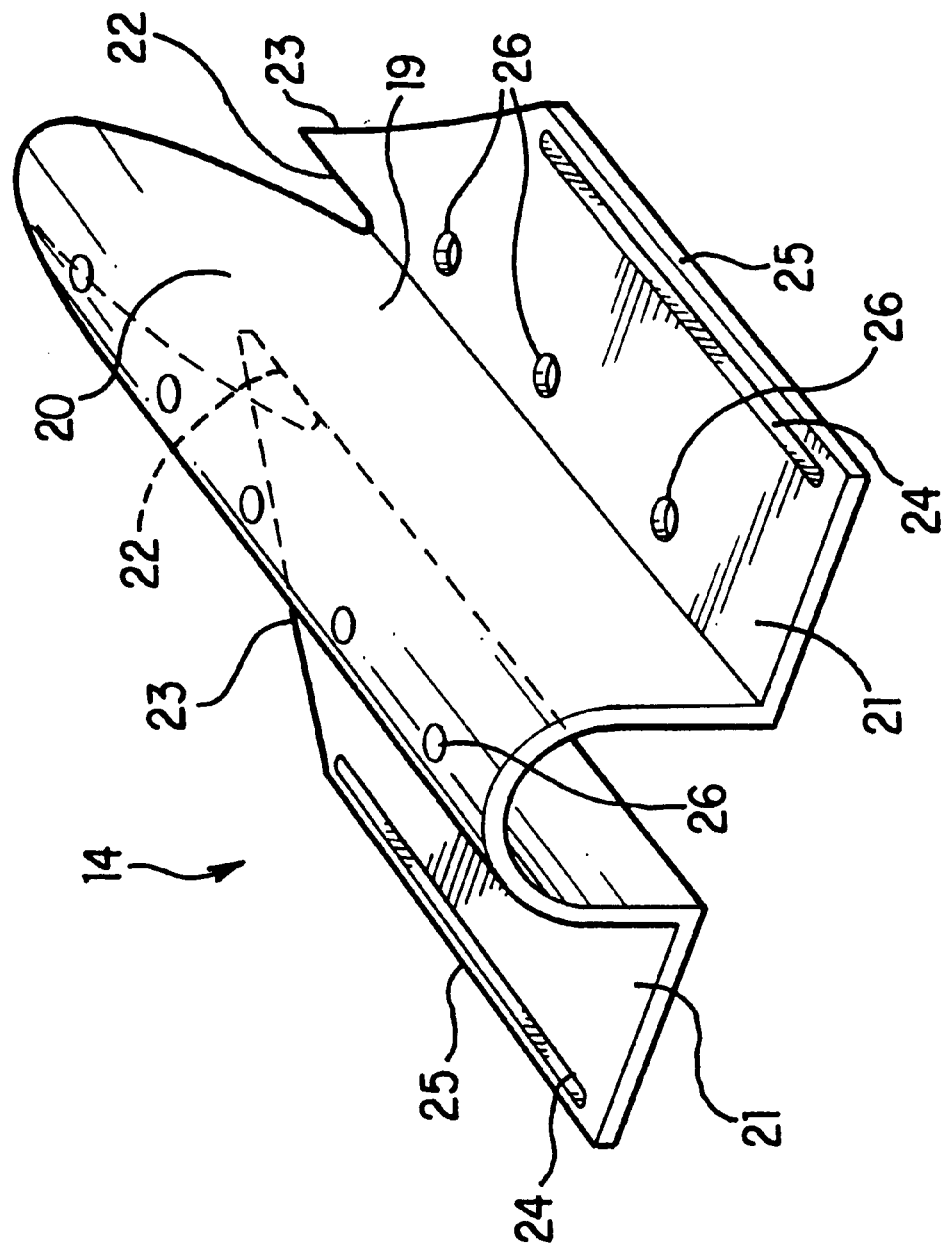
FIG. 3 is a perspective view of the needle immobilizing unit of the present invention.
Figure 5:
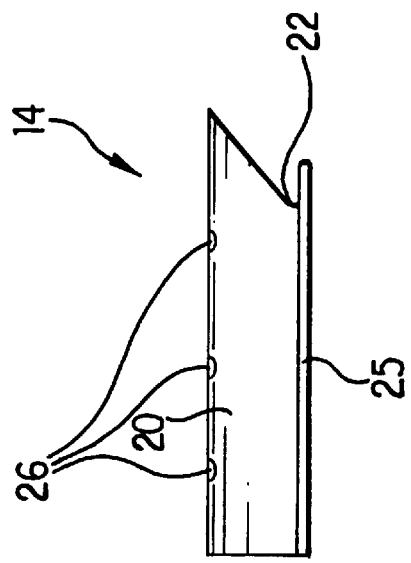
FIG. 5 is a side view of the needle immobilizing unit of the present invention.
Figure 6:
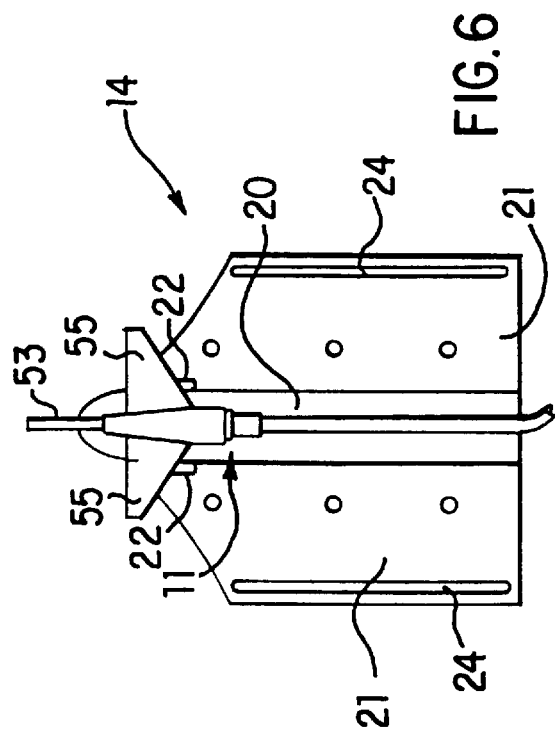
FIG. 6 shows the needle immobilizing unit of the present invention in engagement with the intravascular access device during the therapy.
Figure 4:
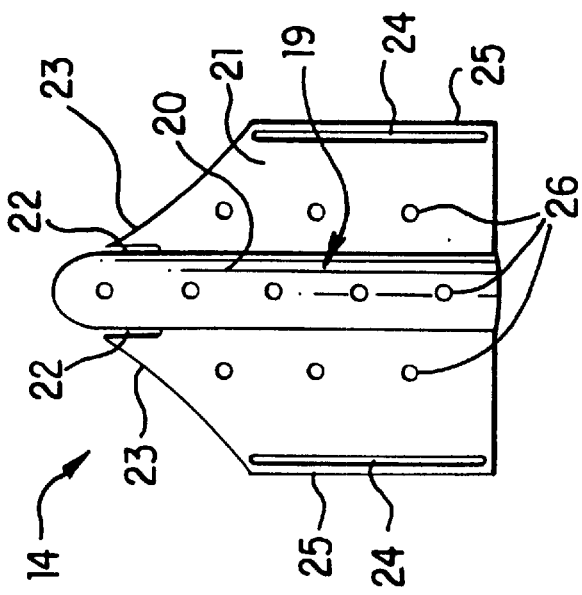
FIG. 4 is a top view of the needle immobilizing unit of the present invention.
Figure 7:
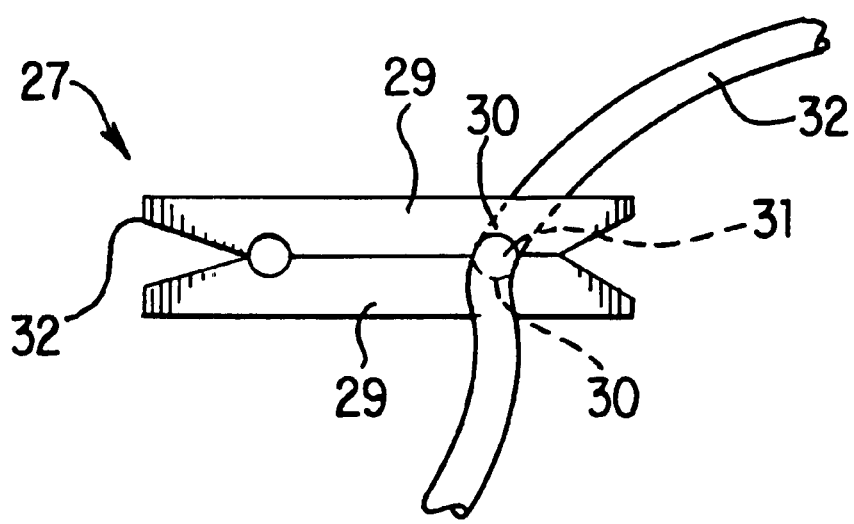
FIG. 7 shows somewhat schematically the tube locking member of the present invention locking the connecting tube therewithin.
Figure 8:
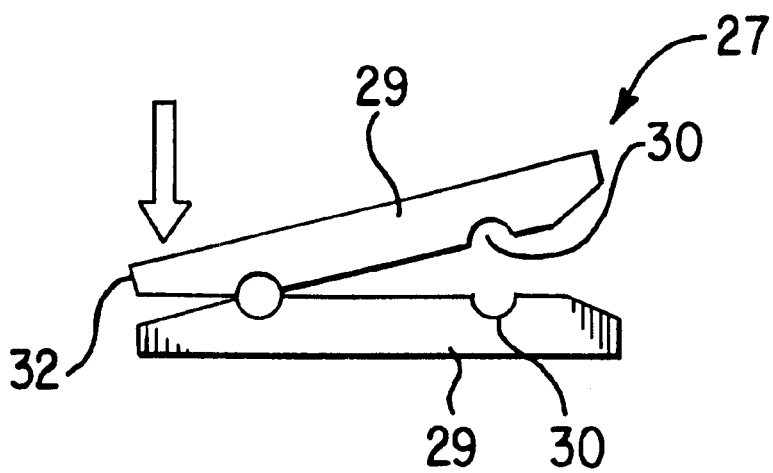
FIG. 8 is a side view of the tube locking member of the present invention in open position.

Referring to FIGS. 1–18, an apparatus 10 of the present invention for maintaining intravascular access device 11 in position at an access point 12 on a limb 13 of a patient includes a needle immobilizing unit 14 (best shown in FIGS. 1–6, and 16–18), a tube locking member 15 (best shown in FIGS. 1, 2, and 7–18), and a strap member 16 (best shown in FIGS. 1 and 16–18) carrying the needle immobilizing unit 14 and tube locking member 15 thereon.

The strap member 16 serves to maintain the needle immobilizing unit 14 and tube locking member 15 on the limb 13 of the patient at a predetermined location, and therefore is adjustable in length to substantially match a circumference of the respective part of the limb of the patient. The adjustability allows a snug fit around the limb 13 during therapy administered to the patient. The strap member 16 may be formed of plastic material or an elastic material which is compatible with the patient's skin. The strap member 16 illustrated in FIG. 1 is a wrist watch type strap with the adjusting mechanism having a plurality of holes 17 and a locking pin 18 which when inserted into a predetermined hole 17 maintains a desired length of the strap member 16.

However, other length adjusting mechanisms for the strap member 16 are contemplated in the scope of the present invention, which may include, but not limited to, Velcro type length adjusting mechanism, latching, clipping, hook- and-loop, male/female fasteners, and other mechanisms known to those skilled in the art capable of adjusting the length of the strap member 16.

The needle immobilizing unit 14 includes a substantially transparent or transparent shield made of a hard clear plastic which has a semi-cylindrical elongated central portion 20 extending longitudinally along the transparent shield 19. A pair of fans 21 extend symmetrically from the central portion 20 in opposite directions, and locking wings 22 formed at the proximal ends 23 of the fans 21. These wings are generally located between the central portion 20 and the fans 21, as best shown in FIGS. 1 and 3–6. Each fan 21 has a slot 24 extending along a side edge 25. The strap member 16 protrudes through the slots 24 to affix the needle immobilizing unit 14 to the strap member 16. A plurality of ventilation holes 26 are disposed on the transparent shield 19 of the needle immobilizing unit 14 for further comfortability of the structure of the present invention when positioned on a patient.

The tube locking member 15, preferably formed of a plastic material, is affixed to the strap member 16 at a predetermined length from the needle immobilizing unit 14. Any one of a number of adhesives known to those skilled in the art which are applicable for medical purposes may be used to glue the tube locking member 15 to the strap member 16. The tube locking member 15 can be made as a clip 27 shown in FIGS. 1, 7, and 8, or as a tube housing unit, best shown in FIGS. 9–15.

The clip 27 has a pair of resiliently biased fingers 29 each having aligned recesses 30 extending transversely across the fingers 29. When the resiliently biased fingers 29 engage with each other the recesses 30 form a tube receiving channel 31 in which the connecting tube 32 of the intravascular device 11 is locked as shown in FIGS. 2, 7, 17 and 18.

In order to lock the connecting tube 32 in the clip 27 or to remove the connecting tube 32 therefrom, a nurse, or any other medical professional administering the therapy to the patient, presses the upper finger 29 at the rear end 32 thereof, thereby disengaging the fingers 29 each from the other, resulting in the opening of the tube receiving channel 31 in order that the connecting tube 32 can be inserted or released therefrom.

In an alternative implementation, the tube locking member 15 constitutes the tube housing unit 28, best shown in FIGS. 9–15, which includes a bottom portion 33, and a top portion 34. Bottom portion 33 and top portion 34 are pivotally joined each to the other at the ends 35 of the bottom portion 33 and the end 36 of the top portion 34 by a leaf 37.

A latching mechanism 38 is positioned at the end 39 of the top portion 34 and the end 40 of the bottom portion 33. The latching mechanism 38 includes a pair of resilient fingers 41 extending from the top portion 34 at the end 39 and a mating recess 42 positioned at the end 40 of the bottom portion 33.

As best shown in FIGS. 12–15, mating recess 42 has a vertical wall 43 provided with extensions 44 which are symmetrically disposed on the vertical wall 43. The extensions 44 form a gap 45 therebetween, as best shown in FIG. 12, and have a ledge 46 on the bottom thereof.

Figure 14:
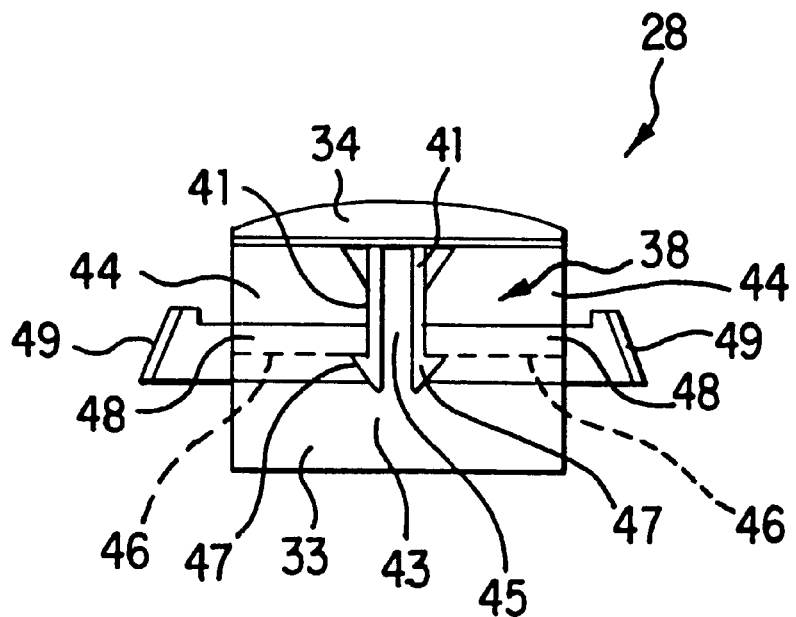
FIG. 14 shows the tube housing unit of the present invention in closed position showing in detail the latching mechanism taken along Lines 14—14 of FIG. 10.

In the closed position, best shown in FIG. 14, the top portion 34 is pressed towards bottom portion 33, so that the resilient fingers 41 are introduced into the gap 45 and engage the ledge 46 of the extensions 44 by the hooks 47 on the ends of the resilient fingers 41. In this manner, the tube housing unit 28 is prevented from being open.

In order to open the tube housing unit 28, a pair of unlocking beams 48 are provided which extend laterally outwardly from the resilient fingers 41. Each unlocking beam 48 is provided at the end thereof with a pressing pad 49 angled with respect to the unlocking pins 48 for the convenience of a nurse administering the therapy.

Figure 15:
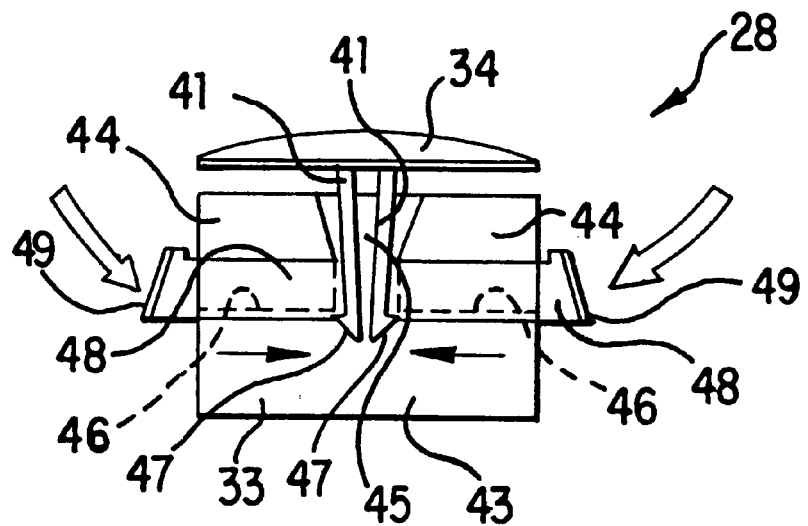
FIG. 15 is a view of the tube housing unit of the present invention taken along Lines 14—14 of FIG. 10 showing schematically transformation of the tube housing unit from the closed position into open position.

When the tube housing unit 28 has to be opened, a nurse, or any other medical professional, presses both pressing pads 49, as shown in FIG. 15 by the directional arrows. Thus, the pressing force is conveyed from the pressing pads 49 through the unlocking beams 48 to the resilient fingers 41, and displaces them towards each other, thereby disengaging the hooks 47 from the ledge 46. This allows the resilient fingers 41 to be lifted from the mating recess 42 through the gap 45. The top portion 34 then can be removed from the top of the bottom portion 33, and the tube housing unit 28 is transferred to the open position.

Figure 9:
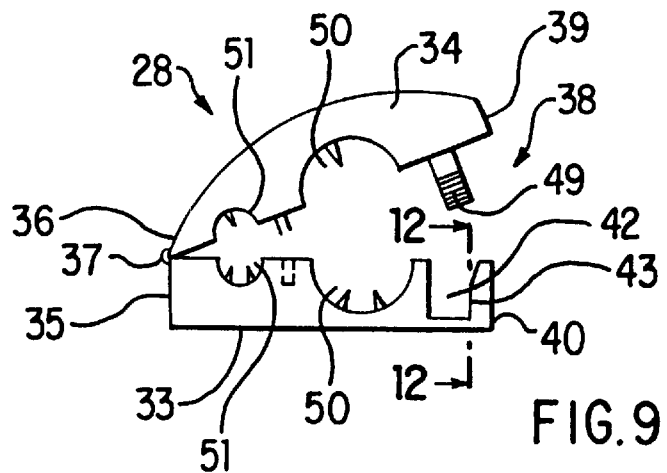
FIG. 9 is a side view of the tube housing unit of the present invention in open position.

As best shown in FIG. 9, the top portion 34 and the bottom portion 33 of the tube housing unit 28 have respective recesses 50 and 51. The recesses on the top portion 34 are aligned with respective recesses on the bottom portion 33, so that in the closed position of the tube housing unit 28, the recesses 50 and 51 form tube receiving channels in which the connecting tube 32 may be captured.

Figure 10:
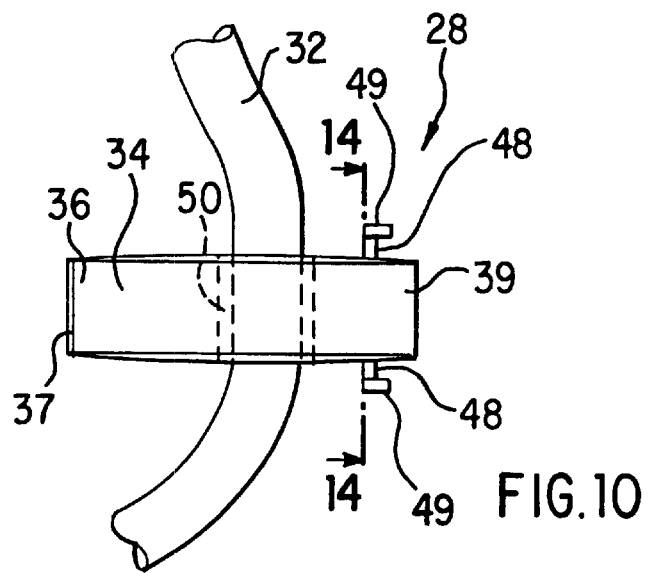
FIG. 10 is a top view of the tube housing unit of the present invention in closed position showing a connecting tube locked within the tube receiving channel.
Figure 11:
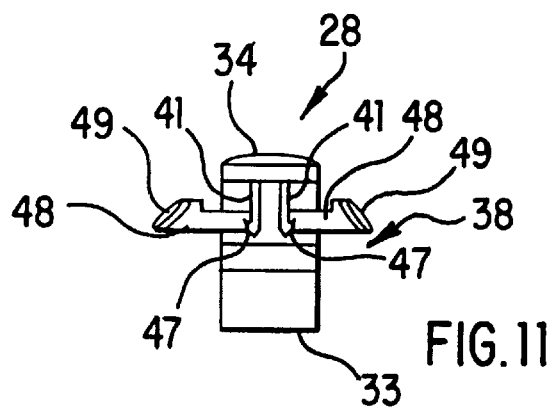
FIG. 11 is a front view of the tube housing unit of the present invention in the open position showing in detail a latching mechanism on the top portion of the tube housing unit.

As best shown in FIG. 9, the recesses 50 form a tube receiving channel for receiving connecting tubes with larger diameter, while the tube receiving channel formed by recesses 51 form a receiving channel for receiving smaller connecting tubes. This feature is however optional, and only one receiving channel may be provided in the tube housing unit 28 laterally crossing the unit 28, as best shown in FIG. 10. The bottom and top portions 33 and 34, respectively, of the tube housing unit 28 are provided with fine teeth 52 within the recesses 50 and 51, which serve for holding the connecting tube 32 within the tube receiving channel immovably and without obstructing the flow within the connecting tube 32.

In use, as best shown in FIGS. 2, 6, 17, and 18, the intravascular access device 11 is positioned on the respective part of the limb of the patient, with the needle member 53 of the intravascular access device 11 introduced into the blood vessel (not shown) through the access point 54. The strap member 16 is then affixed to the limb 13 of the patient in close proximity to the access point 54 with the transparent shield 19 covering the intravascular access device 11. It simultaneously engages the needle wings 55 with the locking wings 22 of the transparent shield 19, thereby locking the intravascular access device 11 in position. The connecting tube 32 is locked within the clip 27 or the tube housing unit 28 as described in previous paragraphs for preventing dislodgement of the needle member 53 from the blood vessel or separation of the connecting tube 32 from the needle member 53.

Although the structure of the present invention assures immobilizing of the intravascular access device 11, it is possible that the needle is dislodged from the blood vessel and starts infusing in the tissue. The doctor or the nurse can readily see any fluid infiltration through the clear cover plastic shield 19. Also, medical personnel may visually ascertain if there is any bleeding and take any precautionary measures to avoid any accidental dislodgement of the needle from the blood vessel or separation of the connecting tube from the needle member.

With the apparatus of the present invention, once the needle member and its connecting tube is fixed, the risk of dislodging the needle member is optimally minimized.

Figure 16:
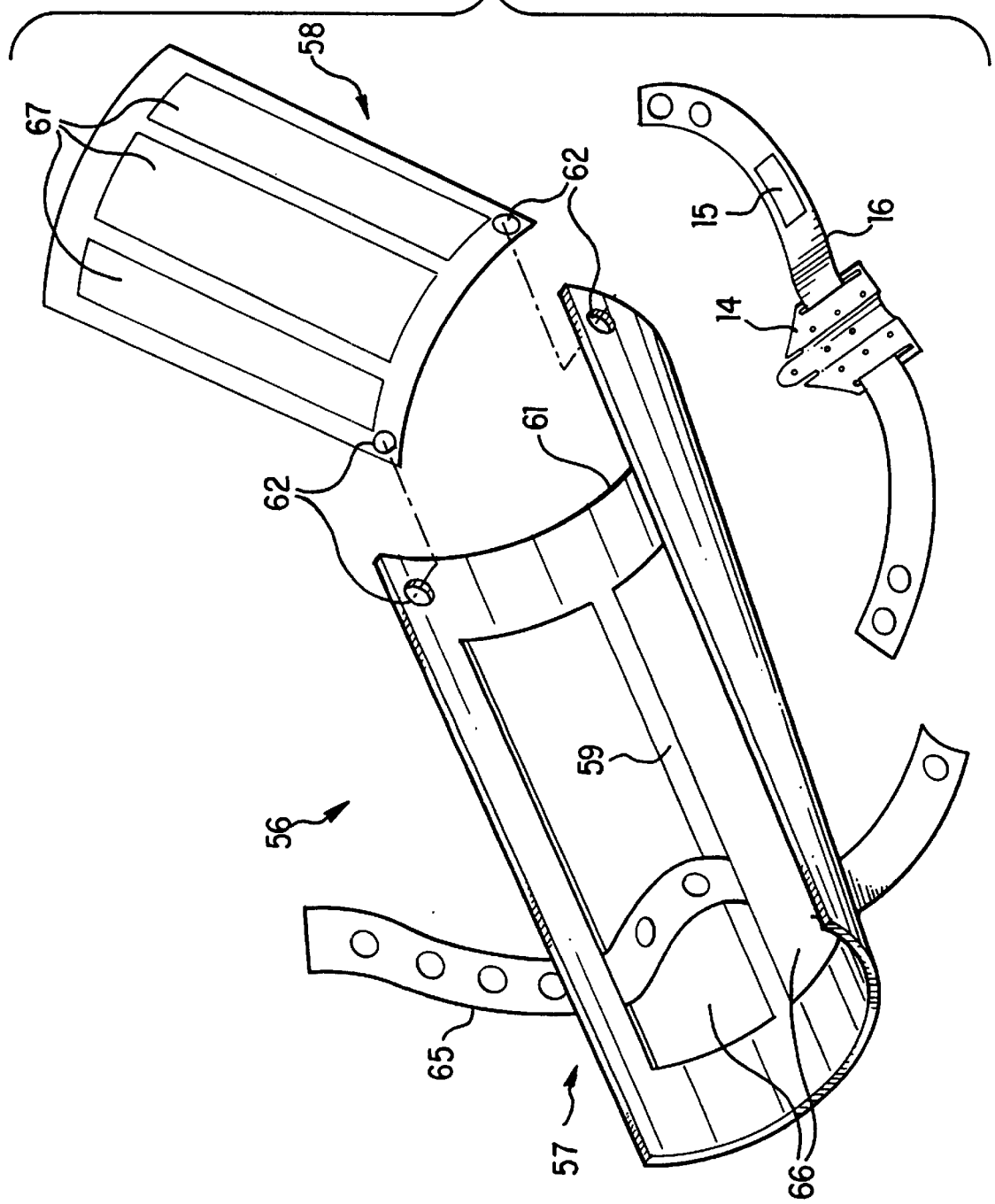
FIG. 16 is a perspective exploded view illustrative of the splint assembly of the present invention.
Figure 17:
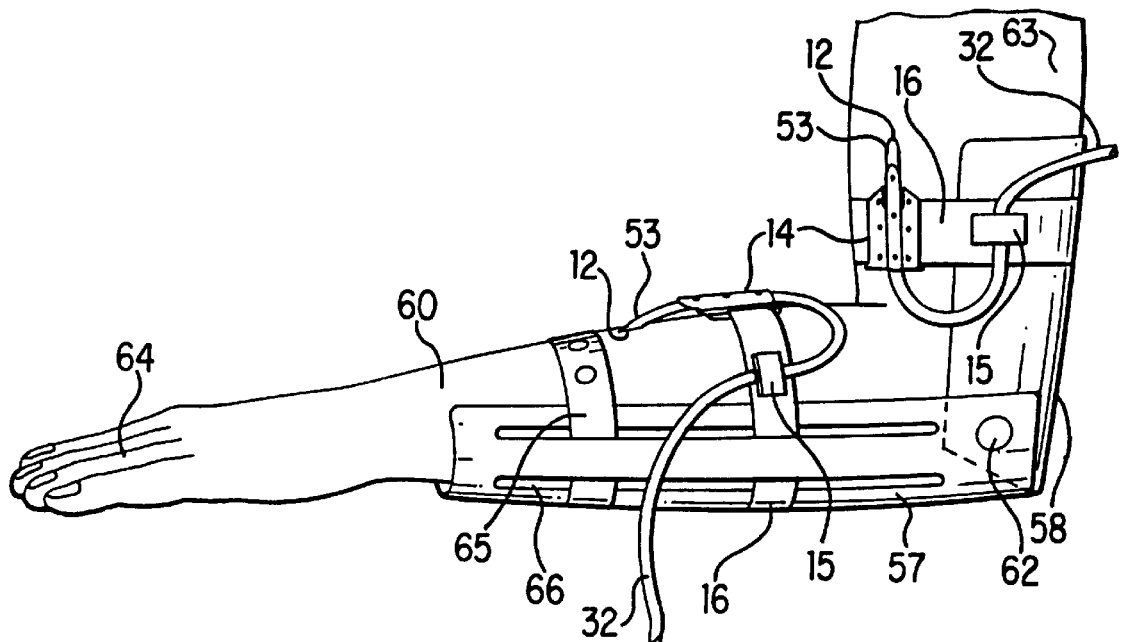
FIG. 17 shows somewhat schematically the splint assembly of the present invention secured to the forearm-arm portion of the limb; and, FIG. 18 shows somewhat schematically the splint assembly of the present invention secured to the forearm-hand portions of the limb.
Figure 18:
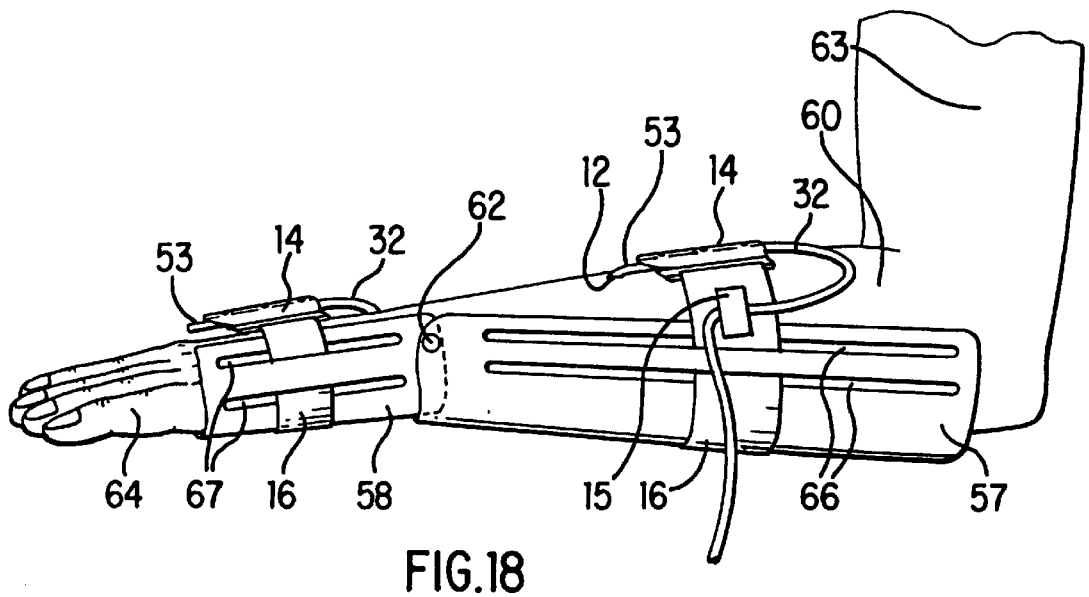

In certain comatose, disoriented or combative patients, an added support is needed for the strap member 16. This support is provided by a strong plastic splint member or splint assembly. Referring to FIGS. 16–18, a hemodialysis and vascular splint, further referred to as a splint assembly 56 of the present invention, includes a forearm splint member 57 and an arm/hand splint member 58.

Both splint members 57 and 58 are formed of a thin, firm, and pliable plastic material or any biocompatible firm pliable material which can support the force loading commensurate with the objects and use of the subject invention. The forearm splint member 57 and the arm/hand splint member 58 are removably coupleable to each other at respective ends thereof, and may be used individually, depending on the need for certain therapy which the patient is undergoing.

The forearm splint member 57 has a semi-cylindrical body 59 which extends approximately 10 inches and has a width of approximately 7.5 centimeters. The semi-cylindrical body 59 of the forearm splint member 57, when affixed to the forearm 60, as best shown in FIGS. 17 and 18, comfortably cradles the forearm 60 around approximately half of the circumference thereof. At the end 61, the forearm splint member 57 is provided with a joint assembly 62 allowing relative pivotal movement about a pivot axis with regard to the arm/hand splint member 58.

The joint assembly 62 includes a pivoting and latching mechanism which provides locking action for securing the forearm splint member 57 in angled relation to the arm/hand splint member 58 at a desired angle therebetween for better comfort of the patient during the therapy. When the splint assembly 56 is used as an arm/forearm assembly, then the splint can be latched at 90°, or other convenient angle. When the forearm/hand assembly is used, then the splint may be locked at 220°, or other appropriate angle.

The joint assembly which provides pivoting and latching action, is known to those skilled in the art, and may include a gear mechanism with an indicator of the angle and a lock latching the gear mechanism at a desired angle. The design of the joint assembly 62 is not discussed in detail herein, since it is not the subject of the invention in question, and is well known to those skilled in the art.

The arm/hand splint member 58 is similar to the forearm splint member 57, with the exception that it is shorter, and is about 6 inches long.

As best shown in FIGS. 17 and 18, the forearm splint member 57 is affixed to the forearm 60 of the patient, while the arm/hand splint member 58, is affixed either to the arm part 63 of the limb of the patient or to the hand 64.

At least one plastic strap 65 is provided for each splint member. The plastic strap 65 serves merely for supporting and immobilizing the splint members on the respective part of the limb 13 of the patient, and therefore are distinguished from the strap member 16 carrying needle immobilizing unit 14 and tube locking member 15.

Although the strap member 16 is also used for securing and supporting a splint member to the respective part of the limb 13, sometimes it is necessary to add a supporting plastic strap 65 for immobilizing of the splint member to the respective part of the limb. The plastic strap 65 is capable of being adjusted in length in order to match the circumference of the respective part of the limb of the patient in order to snugly embrace the limb and to immovably affix the splint member thereto during the therapy.

The plastic strap 65 and the strap member 16 are movable along the longitudinal axis of the forearm splint member 57 and the arm/hand splint member 58. In order to provide sliding movement of the strap 65 and 16 along the splint members, each of the splint members are provided with at least a pair of parallel slots 66 on the forearm splint member 57 and slots 67 on the arm/hand splint member 58. These slots extend along the splint member substantially throughout the length thereof.

Sometimes, during the therapy, two blood vessels of the same part of the limb 13 are to be punctured by intravascular access devices 11. Then, each of splint members is provided with two strap members 16 carrying the needle immobilizing unit 14 and the tube locking member 15. In this situation, the plastic strap 65 is not necessary, since two strap members 16 will securely immobilize the respective splint member to the part of the limb 13.

The splint assembly 56 may be used in a very flexible manner, for example, each splint member 57 and 58 can be used individually for a respective part of the limb 13 of the patient, or both splint members 57 and 58 may be used for the arm/forearm part of the limb. The flexibility of the splint assembly 56 is convenient for a physician or nurse administering the therapy to the patient.

To conduct a procedure, the patient's arm, forearm, or the hand, is cleaned with antiseptic solution. If the patient is well-oriented, awake and alert, then the strap member 16 carrying the needle immobilizing unit 14 and tube locking member 15 is used without the splint assembly 56.

As soon as the needle member 53 is in position in the blood vessel (vein, or the artery, or the shunt in the case of the hemodialysis), the transparent shield 19 is positioned in such a way as to lock and immobilize the needle wings 55 of the needle member 53, i.e., the fans 21 are positioned between the skin of the patient and the needle wings 55. A central portion 20 of the transparent shield 19 covers the intravascular access device 11 and the access point 12.

The strap member 16 is then adjusted so that it fits snugly to the respective part of the limb 13. There are many ways to adjust the strap member 16, as described in previous paragraphs. After the needle member is immobilized by means of the needle immobilizing unit 14, the connecting tube 33 is locked within the tube housing unit 28 or the clip 27 and impedes separation of the connecting tube 32 from the needle member 53.

The needle member 53 and the connecting tube 32 are, therefore immobilized, so that any dislodgement of the needle member from the blood vessel is prevented. However, if a dangerous situation of bleeding or tissue infusion occurs, the nurse or the doctor can visually ascertain the bleeding since the shield 19 is transparent.

In certain comatose, combative, or disoriented patients, an extra precaution is added which is the splint assembly 56. The splint assembly will immobilize the elbow joint, or the wrist joint. The plastic splint must be hard enough to receive the part of the arm, or the forearm. The locking mechanism of the splint between the splint members 57 and 58 must be strong enough to withstand the power of the elbow joint or the wrist joint. The splint itself is strong enough to be used as an added precaution to insure that the patient does not avulse the intravascular access unconsciously.

If the blood vessel to be punctured is situated in the arm, then the arm/hand splint member is used. If the blood vessel to be punctured is situated in the forearm part of the limb 13, then the forearm splint member 57 is used. If the blood vessel used is located near the elbow joint, or a blood vessel is in the arm part, and another blood vessel is in the forearm part, then the arm splint member and the forearm splint member are used, as shown in FIG. 17.

If the blood vessel to be punctured is located near the wrist joint, then the hand/arm splint member 58 is utilized. If two blood vessels are needed for access, one near the wrist joint and the other in the middle of the forearm part, then the hand/arm splint member 58 and the forearm splint member 57 are used.

Once the blood vessel is punctured by the needle member 53 (which may be a needle, catheter, or other tube allowing puncturing through a vessel wall), the splint assembly 56, which comprises one or both splint members 57 and 58 in required disposition thereof, is positioned on the limb of the patient. The strap member 16 is moved along the respective splint member towards an access point 12 on the part of the limb, and when the strap member 16 reaches the proximity to the access point 12, the length of the strap member 15 is adjusted by means of the adjusting mechanism described in previous paragraphs, to match the circumference the respective part of the limb of the patient. The needle immobilizing unit 14 and the tube locking member 15 are used to immobilize the intravascular access device 11. If the strap member 16 is not sufficient for securing the splint member or the splint assembly to the limb, the plastic strap 65 which is merely a supporting strap, is used, which has a length adjusting mechanism similar to the strap member 16.

All straps used in the arrangement, provide comfortable although tight encircling of the respective part of the limb 13 of the patient. When all straps on all required splint members are positioned in the proximity to the access point 12 on the limb 13, and locked to snugly fit around the part of the limb, the splint members 57 and 58 are immovably affixed to the respective part of the limb 13. The arm or hand is cradled within the semi-cylindrical body of the arm/hand splint member 58, and/or forearm comfortably received in the semi-cylindrical body of the forearm splint member 57.

The joint assembly 62 can be set in a required angular position before the splint assembly is put on the limb of the patient, or after when the splint assembly is already in position on the limb 13. In either case, the angle between the splint members 57 and 58 is adjusted and latched in a desired angled interposition therebetween which is the most comfortable position for the patient.

The apparatus of the present invention may find utility in any intravascular access procedure, and especially will be useful when the therapy lasts for extended periods of time, as during hemodialysis, where patients need an intravascular access at least 2–3 times each week and for three or more hours for each procedure. Using the device of the present invention will provide needed safety for a patient, since any movement of the patient will neither dislodge the needle from the blood vessel or separate the connecting tube from the needle.

Although this invention has been described in connection with specific forms and embodiments thereof, it will be appreciated that various modifications other than those discussed above may be resorted to without departing from the-spirit or scope of the present invention. For example, equivalent elements may be substituted for those specifically shown and described. Certain features may be used independently of other features, and in certain cases, particular locations of elements may be reversed or interposed, all without departing from the spirit or scope of the invention as defined in the appended claims.

What is claimed is:

1. An apparatus for maintaining intravascular access device in position at an access point on a limb of a patient, said intravascular access device including a needle member introduced into a blood vessel and a connecting tube coupled to said needle member, said apparatus comprising:
   a needle immobilizing unit engaging said needle member and preventing the same from dislodgement from the blood vessel;
   a tube locking member immobilizing said connecting tube in place and preventing the same from being separated from said needle member;
   a supporting structure supporting said needle immobilizing unit in substantial proximity to the access point on the limb of the patient, and further supporting said tube locking member, said supporting structure including a strap member encircling a respective part of the limb of the patient, and means on said strap member for adjusting the length thereof to substantially match a circumference of the respective part of the limb of the patient; and,
   at least one splint member affixable to the respective part of the limb of the patient by said strap member slidable along said at least one splint member.

2. The apparatus of claim 1, further including a second splint member pivotally releasably engaged with said at least one splint member at respective ends thereof, and another said strap member, said second splint member being affixable to another respective part of the limb of the patient by said another strap member slidable therealong.

3. The apparatus of claim 2, wherein said at least one splint member is a forearm splint member, and said second splint member is an arm splint member.

4. The apparatus of claim 2, wherein said at least one splint member is a forearm splint member, and said second splint member is a hand splint member.

5. The apparatus of claim 1, further including at least one supporting strap having adjustable length and immovably supporting said at least one splint member at the respective part of the limb of the patient.

6. An apparatus for maintaining an intravascular access device in position at an access point on a limb of a patient, said intravascular access device including a needle member introduced into a blood vessel, a pair of wing members extending from said needle member, and a connecting tube coupled to said needle member, said apparatus comprising:
   at least one splint member;
   at least one strap member slidable along said at least one splint member and securing the same to a respective part of the limb of the patient;

a second splint member pivotally releasably engaged with said at least one splint member at respective ends thereof;

at least a second strap member securing said second splint member to another part of the limb of the patient;

first means for immobilizing said intravascular access device in position on the respective part of the limb of the patient, said first immobilizing means being affixed to said at least one strap member and including means for engaging said wing members of said intravascular access device; and, second immobilizing means for immobilizing a second intravascular access device, said second immobilizing means being affixed to said second strap member.

7. The apparatus of claim 6, wherein said at least one splint member is a forearm splint member, and said second splint member is an arm splint member.

8. The apparatus of claim 6, wherein said at least one splint member is a forearm splint member, and said second splint member is a hand splint member.

9. The apparatus of claim 6, further including a joint assembly releasably coupling said at least one splint member to said second splint member, said joint assembly including a latching mechanism locking said at least one and said second splint members in a desired angled relationship therebetween.

10. The apparatus of claim 6, wherein said at least one splint member includes at least one slot extending longitudinally along the length of said at least one splint member, said strap member being slidable along said at least one slot to position said intravascular access device relative to said at least one splint member.

11. A method for maintaining an intravascular access device in position at an access point on a limb of a patient during therapy, said intravascular access device including a needle member introduced into a blood vessel aid having needle wings, and a connecting tub e coupled to said needle member, said method comprising the steps of:

providing a strap member carrying a needle immobilizing unit and a tube locking member thereon;

positioning said strap member adjacent to the access point on the limb of the patient and adjusting the length of said strap member to substantially match a circumference of the limb of the patient;

locking said needle member at the access point on the limb of the patient by capturing said needle wings with said needle immobilizing unit;

locking said connecting tube in place by means of said tube locking member, thereby preventing displacement of said intravascular access device;

providing a first splint member, affixing said first splint member to a respective part of the limb of the patient;

securing said strap member to said first splint member;

providing a second splint member and coupling said first and second splint members at respective ends thereof, securing a second strap member carrying another said needle immobilizing unit and another said tube locking member thereon to said second splint member;

affixing said second splint member to another respective part of the limb of the patient; and locking another intravascular access device in position on the another respective part of the limb of the patient by means of said another needle immobilizing unit and said another tube locking member.

12. The method of claim 11, wherein said step of providing a second splint member and coupling said first and second splint members includes the step of latching said first and second splint members at a desired angular disposition therebetween.

* * * * *